US008881980B2

(12) United States Patent
Magill (10) Patent No.: US 8,881,980 B2
(45) Date of Patent: Nov. 11, 2014

(54) APPARATUS FOR VERIFYING THE IDENTITY OF A FINAL FLUID PRODUCT FOR MEDICAL OR PHARMACEUTICAL USE

(75) Inventor: Conan Magill, St Albans (GB)

(73) Assignee: STEPRA Ltd., Luton (GB)

( * ) Notice: Subject to any disclaimer, the term of this patent is extended or adjusted under 35 U.S.C. 154(b) by 281 days.

(21) Appl. No.: 13/387,848

(22) PCT Filed: Aug. 4, 2009

(86) PCT No.: PCT/EP2009/060071
§ 371 (c)(1),
(2), (4) Date: Jan. 30, 2012

(87) PCT Pub. No.: WO2011/015228
PCT Pub. Date: Feb. 10, 2011

(65) Prior Publication Data
US 2012/0125998 A1 May 24, 2012

(51) Int. Cl.
*G06K 7/00* (2006.01)
*G01N 21/65* (2006.01)
*G01N 21/33* (2006.01)
*G01N 21/25* (2006.01)
*G01N 21/35* (2014.01)

(52) U.S. Cl.
CPC .............. *G01N 21/65* (2013.01); *G01N 21/33* (2013.01); *G01N 21/25* (2013.01); *G01N 21/359* (2013.01); *G01N 2201/0221* (2013.01); *A61M 2205/60* (2013.01); *A61M 2205/6063* (2013.01); *A61M 2205/3313* (2013.01)
USPC ........... 235/385; 235/375; 235/380; 235/435; 235/439; 235/462.01

(58) Field of Classification Search
USPC .......... 235/375, 380, 383, 435, 439, 454, 462
See application file for complete search history.

(56) References Cited

U.S. PATENT DOCUMENTS

| 4,884,065 A * | 11/1989 | Crouse et al. ................. 340/632 |
| 2007/0201025 A1* | 8/2007 | Greenwald ................... 356/319 |
| 2008/0214925 A1* | 9/2008 | Wilson et al. ................ 600/410 |
| 2009/0178857 A1* | 7/2009 | Yuyama et al. ............ 177/25.13 |

FOREIGN PATENT DOCUMENTS

| EP | 0 346 548 A1 | 12/1989 |
| EP | 1 433 456 A1 | 6/2004 |
| WO | 03/100416 A1 | 12/2003 |

OTHER PUBLICATIONS

International Search Report, dated May 20, 2010, from corresponding PCT application.

* cited by examiner

*Primary Examiner* — Matthew Mikels
(74) *Attorney, Agent, or Firm* — Young & Thompson (57) ABSTRACT

An apparatus (22) for verifying a final product being packaged in a final container (28), includes an optical spectroscopy analysis unit including a device for holding the final container (28), and a probe, characterized in that the holding device includes a clamping system including a reference platform (32) for supporting and positioning the final container (28) in a determined position with respect to the probe (P) and a clamping bar (36), the holding device being adapted to receive any form of final containers such as syringes, vials or Intravenous bags. In addition, a software for managing and characterizing optical signals from a drug product to confirm that the drug was correctly prepared prior to administration is described.

18 Claims, 8 Drawing Sheets

APPARATUS FOR VERIFYING THE IDENTITY OF A FINAL FLUID PRODUCT FOR MEDICAL OR PHARMACEUTICAL USE

TECHNICAL FIELD OF THE INVENTION

The present invention concerns an apparatus for a computerized spectroscopy (Preferably using the Raman effect) system and associated with a method for performing a spectrographic analysis of a known drug to be injected, for the purpose of confirming the drug's identity, concentration, and total dose being delivered, thus providing a quality control step in the overall preparation of compounded sterile products for hospitals, clinics, and other places where these products are prepared for patient administration.

Such an apparatus permits the analysis to be performed on a drug sample to be injected while it is contained within a final drug delivery container or package such as an IV bag, a vial or a or syringe.

BACKGROUND OF THE INVENTION

Complications arising from medicines treatment are the most common cause of adverse events in hospital patients and generate adverse publicity for the concerned health service. Errors may occur from the initial decision to prescribe to the final administration of the medicine, and include choice of the wrong medicine, dose, route, form, and/or frequency or time of administration. In the United Kingdom, the National Patient Safety Agency has received 71,000 medicines incident reports since 2001.

The drug use process includes the prescribing, transcribing, manufacturing or compounding, dispensing and administration of a drug, and monitoring therapy. Intravenous therapy is complex and high risk and usually requires the manipulation of a medicine before administration to the patient. There have been deaths and harm following intravenous therapy due to administration of the wrong drug, dose, route and diluent. Clinical studies have identified very high error rates in preparing and administering intravenous medicines in hospitals.

The process of preparing an intravenous medicine for administration involves correct interpretation of a prescription; correct drug calculation; selection of the correct drug, strength, form, reconstitution fluid, diluent and final container; use of appropriate equipment and technique during preparation; correct labelling of the final product; and correct administration including use of an IV pump. At each stage, errors can occur with the potential to cause harm to patients.

The final check before the prepared medicine is 'released' for administration to the patient involves checking any calculations, inspection of the products used in preparation and assessment of the final product including labelling. Quantitative assays of final products are never performed in clinical areas and rarely in pharmacy prepared doses. As a result, the true error rate and therefore harm caused is unknown.

Pharmacists and nurses who are responsible for the final preparation and dilution of drug products to be injected prior to their administration to a patient are charged with performing a final check of the prepared product prior to its administration. However, if the final check is performed by the same person who prepared the product, any error that may have occurred in the course of the drug preparation, i.e. selection of the wrong drug product, errors in the calculation of the required drug dose or diluents to be added, mislabelling of the package or container, etc., are prone to being missed a second time during the check.

If the product is checked by another individual, the checking is difficult to perform, as the second individual is looking at a clear liquid within an IV bag or a syringe, and being asked to confirm that the correct clear liquid was added to another clear liquid in exactly the correct volume to produce the final product.

Other systems have been introduced to this process which either involve the removal of a sample of the final drug package in order to evaluate that sample within special sampling reservoirs by NIR (Near Infra Red) spectroscopy. Another system integrates extensive software and workstations to identify the weights of intermediate preparation steps and barcodes of products selected during the preparation process to guarantee that the correct product is produced. However, this system is difficult to achieve, especially on all of the patient care areas where many drug products are prepared.

This apparatus should permit to reduce medication errors and therefore improve patient safety. In November 2005, a study carried out by the National Audit Office in the United Kingdom found that 2081 people had died due to medication errors. And over 980,000 patient safety incidents had been reported.

According to the National Patient Safety Agency "the research indicates that the incidence of errors in prescribing, preparing and administering medicines to be injected is higher than for other forms of medicine. In one study, at least one error in 49% of intravenous medicine doses prepared and administered on hospital wards; 1% of errors were judged to be potentially severe; and 29% potentially moderate errors." (NPSA, March 2007)

Currently there exists no system for verifying that the correct cytotoxic drugs have been selected and prepared according to a doctor's prescription. There are no means to go back later and prove that what was prepared was done correctly. Some systems are currently seeking to deploy cameras to provide photographic evidence that the correct drug was utilized and scales inserted into the process to confirm through intermediate weighing steps, that the correct amount of drug was added to an IV bag or syringe. These steps are costly and time consuming, but are indicative of the level of concern that has arisen.

In addition to the errors that are caused by medical personnel preparing cytotoxics, one can regularly read about concerns by regulatory agencies over the integrity of the supply chain within which our drug products are produced and often imported. Counterfeit drugs are a source of concern for most governments, and there is little to no process by which hospitals have technologies that can identify compromised drug products.

It is believed that the successful development of a new apparatus for the "Final Check" in the preparation of cytotoxics within health systems will provide the following:

a. An affordable means to rapidly validate the integrity of a chemotherapy preparation before the drug is sent to the patient care area for administration.

b. A system that does not require sample preparation and can be performed within the prepared packages to be sent to the patient care area.

c. A system whose results can generally be obtained in less than 15 seconds d. A system which can be operated by reasonably low level technical personnel with minimal training required.

BRIEF SUMMARY OF THE INVENTION

The invention proposes an apparatus for verifying the identity (and possibly the concentration) of a final fluid product for medical or pharmaceutical use (of determined composition and/or in determined quantities), said final product being packaged in a final container (such as a syringe, an IV bag or a vial), said apparatus comprising at least an optical spectroscopy analysis unit adapted to determine at least one property of the final product and for issuing at least a verifying signal corresponding to said property, said unit comprising:

a device for holding said final container;

a probe associated with a source of light located and configured so as to emit and direct light through the wall of the final container and the final product and comprising a light sensor located so as to receive said directed light after the light has passed through the final product, said sensor providing light sensor signals to be used for the generation of said verifying signal corresponding to said property;

characterized in that said holding device comprises:

a clamping system comprising a reference platform (or reference plate) for supporting and positioning the final container in a determined position with respect to the probe and a clamping bar which is moveable with respect to the reference platform for pressing the outer wall of the final container in contact with said reference platform, said reference platform being capable of receiving light from said light source, said holding device being adapted to receive any form of final containers such as syringes, vials or IntraVenous bags (IV bags).

The apparatus is preferably associated with a library of representative known signatures of compounds, said library being contained within a computer system which can be accessed to confirm that the prepared drug's signature matches that of the expected drug product within the library.

Other features are defined in the appending claims.

BRIEF DESCRIPTION OF THE DRAWINGS

Other features and advantages of the invention will become apparent from reading the detailed description of the invention with reference to the drawings comprising the following figures in which.

DETAILED DESCRIPTION OF THE DRAWINGS

By way of non-limiting example, with a view to facilitating comprehension of the description, claims and drawings, the terms vertical, upper, lower, horizontal, longitudinal and transverse will be used, without implying any limitation, with reference to the trihedron V, L, T (Vertical, Longitudinal, Transversal) shown in the figures.

Figure 1:
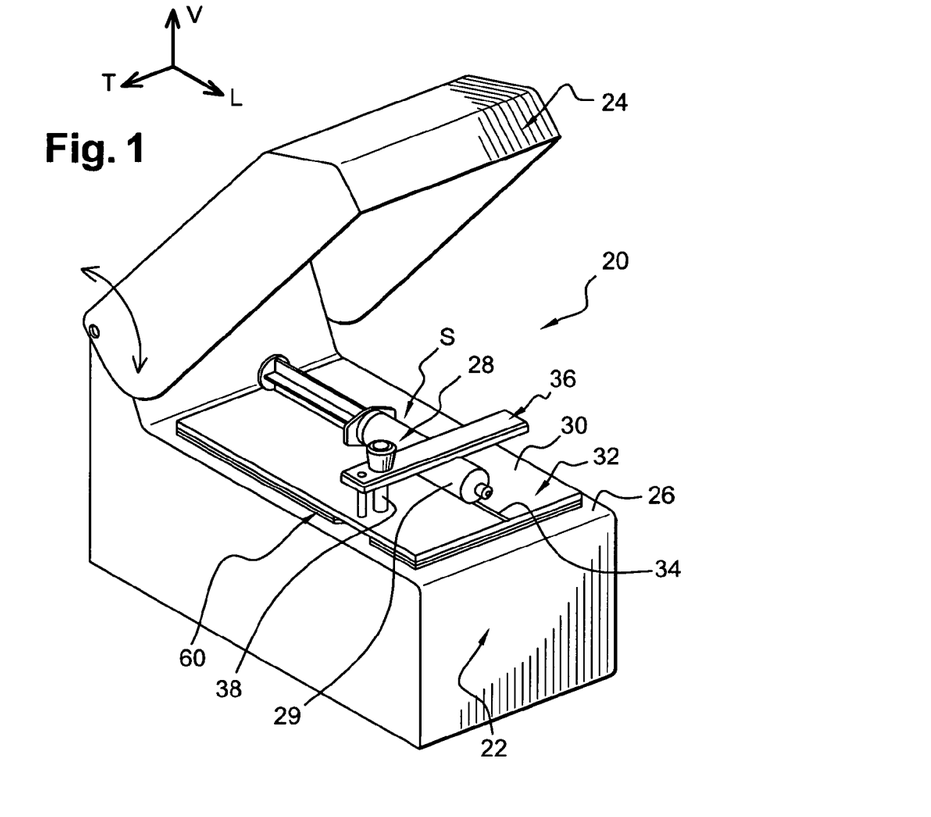
FIG. 1 is a perspective view of a first example of an apparatus according to the invention with its upper pivotal lid in an open position.

FIG. 1 represents an apparatus 20 comprising a lower base 22 of a generally parallelepipedic shape and an upper lid 24 which is here a pivotal lead which is articulated at its rear end around a horizontal axis. The lid 24 is represented in an open position and it can be closed downwardly. In the closed position of the moveable lid, the "optical" conditions inside the apparatus in the analysis zone are identical to those available "in the dark".

When it is in its closed position, the lid 24, in combination with the upper horizontal face 26 of the base 22, encloses a space which contains various elements and components of an analysis unit adapted to determine various properties of a final product which is contained in a final container, or package, such as the syringe "S" illustrated at FIG. 1.

The design also permits the handling and holding of "final" containers wrapped in overwrap bags.

Here, the syringe S contains the sample of a liquid product to be verified in its body 28 which is a rigid cylinder 28 which is horizontally supported on the upper face 30 of a horizontal reference platform 32.

The upper facer 32 is provided with a longitudinal V-shaped groove 34 which participates to the transversal positioning of the outer convex cylindrical wall 29 of the body 28 with respect to the reference platform 32.

The platform 32 cooperates with a clamping bar 36, or clamping "jaw", for holding and pressing the syringe S in its illustrated position where its outer wall 29 is pressed in contact with the upper face 30. The clamping bar 36 secures the position of the syringe, or of an IV bag or of a vial in order to provide for repeatable positioning and consistent verification results.

The clamping bar 36, together with the platform 32, is part of a clamping system. The clamping bar 36 is here pivotally and slidably mounted with respect to the platform 32 along a vertical axis A-A which is transversally offset with respect to the groove 34.

Figure 3:
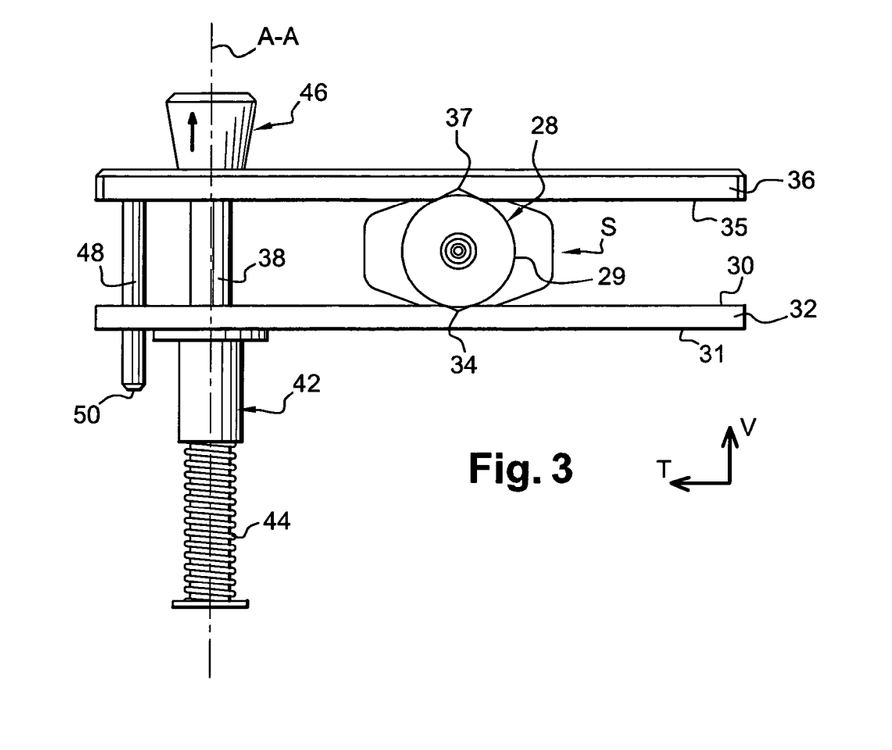
FIG. 3 is a view similar to that of FIG. 2 with the clamping bar in its offset rest angular position.

To this end, the clamping bar 36 is supported at the upper end of a vertical shaft 38 which can pivot and slide through a hole 40 of the platform 32 and which is guided in a guide 42 arranged under the lower face 31 of the platform 32 (see FIG. 3).

A compressed return helical spring 44 is provided in order to permanently urge the shaft 38 and the clamping bar 36 downwardly with respect to the platform 32. Thus, when it is in its work position, the clamping bar 36 is acting with the platform 32 as a clamp, or as a pair of jaws, for pressing the body 28 of the syringe S downwardly.

The shaft 38 and the clamping bar 36 are provided with a handle 46 for permitting a user to move the clamping bar 36 vertically along the axis A-A against the action of the spring 44.

Figure 2:
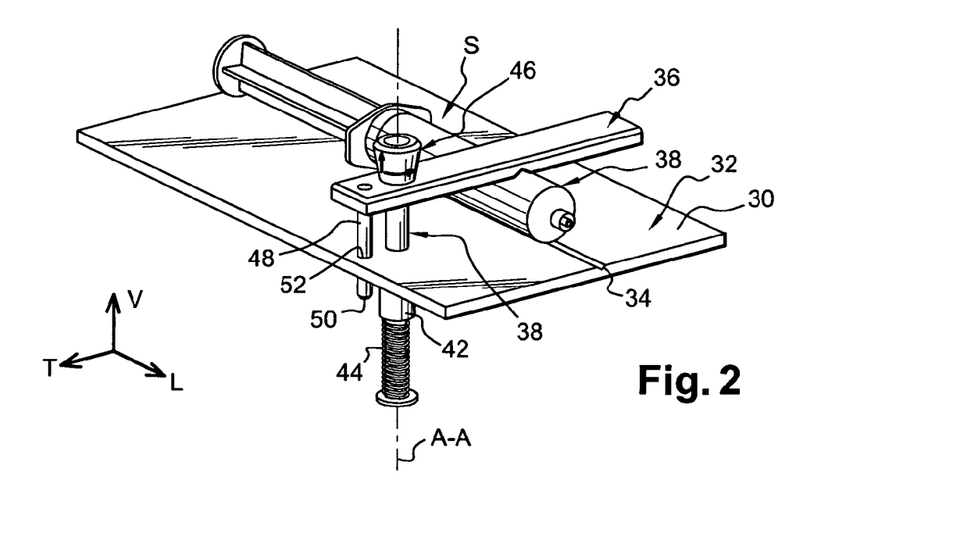
FIG. 2 is a simplified view on an enlarged scale of FIG. 1 showing the clamping system with a syringe in the verifying position and the clamping bar in its angular work position.
Figure 4:
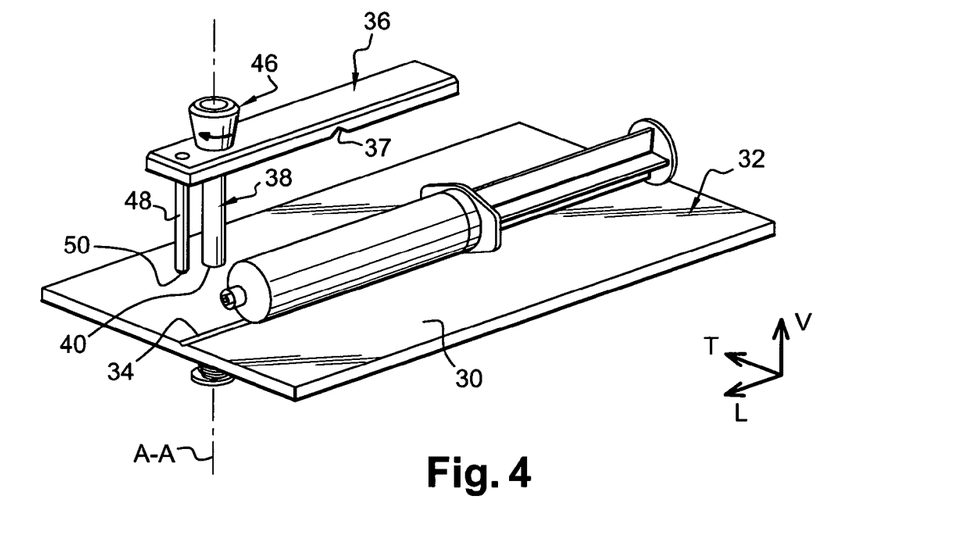
FIG. 4 is a longitudinal end view of FIG. 2.

The handle 46 also permits to pivot the clamping bar 36 around the axis A-A in both senses between its clamping work angular position illustrated at FIGS. 1 to 3, and its offset rest angular position illustrated at FIG. 4 where the syringe S can be placed in position for verification, or taken away from this position.

In its work position, the clamping bar 36 extends transversely in registration with a facing portion of the wall 29 of the body 28 of the syringe S in order to permit its clamping. In order to facilitate the clamping and positioning of cylindrical body of a final container, the lower face 35 of the clamping bar 36 is also provided with a V-shaped groove 37 which is aligned with the groove 36 when the bar is in its work position (see FIG. 3).

In its rest position, after a rotation of 90 degrees, the clamping bar 36 extends longitudinally.

The end of the clamping bar 36 which is close to the shaft 38 is provided with a stem 48 which extends vertically and downwardly from the lower face 35.

The stem 48, together with a through hole 52 provided in the platform 32, is part of a device for angularly locking the clamping bar 36 in its work angular position illustrated at FIGS. 1 to 3 where the lower portion of the stem 48 extends through the hole 52 thus preventing any rotation of the clamping bar 36, while permitting its free vertical movements along the axis A-A.

Starting from the position illustrated at FIG. 2, and in order to pivotally unlock the clamping bar 36, the user starts by pulling upwardly the handle 46 until the stem fully extends out of the hole 52 and with its lower free extremity 50 extending upwardly over the plane of the upper face 30. Then the user pivots the handle in a counter clockwise direction in order to place the clamping bar 36 in its rest angular position of FIG. 4 in which the extremity 50 rests on the upper face 30 thus also maintaining the clamping bar 36 in an upper position, against the returning action of the spring 44.

Figure 5A:
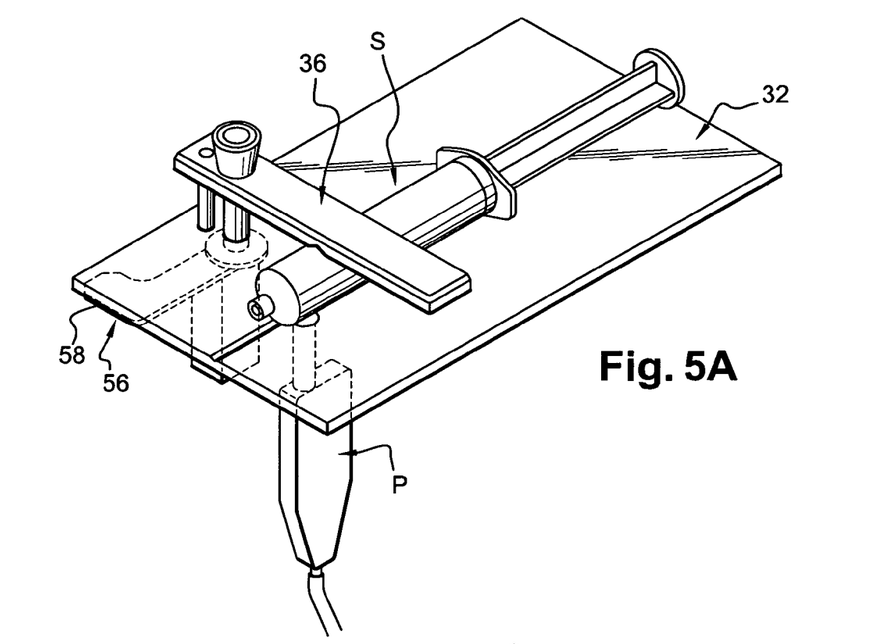
FIGS. 5A and 5B are two figures similar to FIGS. 2 to 4 showing in transparency the moveable mask for the light in its non-masking and masking positions respectively.
Figure 5B:
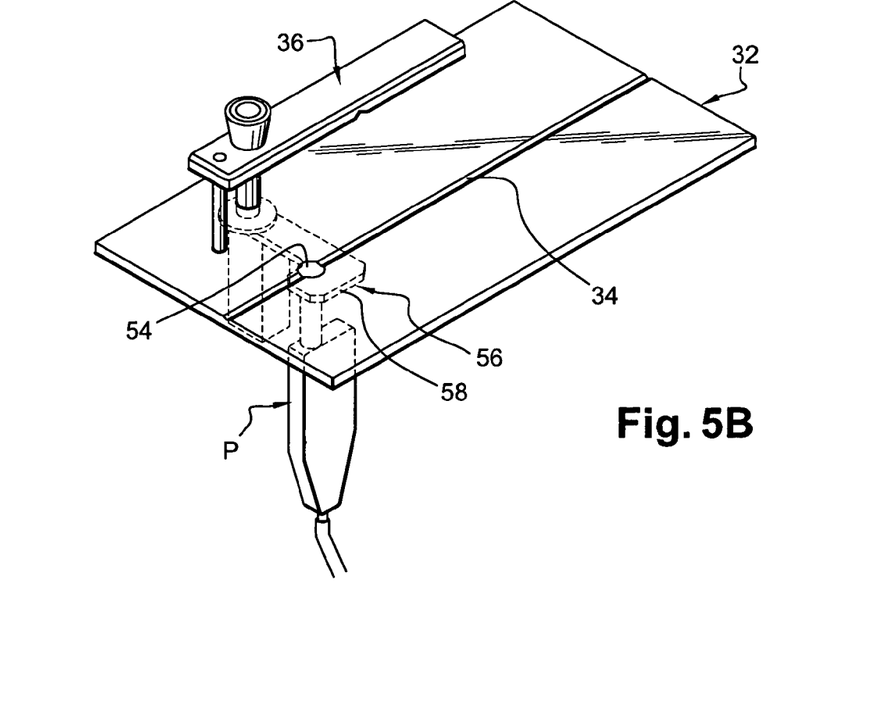

As illustrated for instance at FIGS. 5A and 5B, the platform 32 is provided with a functional through hole 54 which extends vertically, here in registration with the groove 34.

A probe "P", the function of which will be explained later in details, is arranged under the reference platform 32 and positioned so that it is in registration with the functional "analysis" hole 54. The probe P at least permits the emission of an incident beam (or excitation radiation), not illustrated, vertically through the hole 54, which is for instance a laser beam.

The apparatus is here (FIGS. 5A and 5B) provided with a moveable safety mask (or shield) 56 which is pivotally linked with the clamping bar 36 and which, when the clamping bar 36 is in its rest angular position, extends on the way of the hole 54 and thus on the way of the exciting light or beam in order to prevent that such light might be emitted outside beyond the platform 32. To this end, the mask 56 which is arranged under the platform, 32 has here an "L" shape comprising a masking pivoting branch 58.

An other and/or complementary safety device, that is not illustrated, is a switch which is provided in combination with the moveable lid 24 so that it permits emission of light or beam only when the lid is its fully closed position. The lid or cover flap thus acts both to reduce background noise from ambient light sources, as well as a safety switching device according o which the laser source cannot be activated unless the lid is closed.

As a non illustrated variant, all the movements and displacements of the clamping bar 36 with respect to the reference platform 32, as well as those of the moveable lid 24 can be motorized and controlled by an associated software.

According to one aspect of the invention, with a view to permitting to verify and validate medications prior to their administration by allowing a user to validate the medication administered, in composition and quantity—dosage. (Final Checking) the apparatus might integrate a weighing unit, which is for instance a digital load cell (scale), into the sample holding device such that an information or signal representative of the weight of the sample can be collected and that the software can determine, directly or indirectly by calculation, a total weight of the fluid within the final container positioned on the platform 32, thus inferring for instance the total volume of the final product contained in the final container.

Thus, when one knows the concentration (from the spectroscopy analysis system) and the volume of the drug product (from the weighing unit), the total dose of drug to be delivered can be calculated and used as a further (Final) confirmation check. (Of course the tare weight of an empty final container would be subtracted from the weight obtained of the product on the holding device).

Such a weighing unit is schematically illustrated at FIG. 1 in the form of a planar element 60 which is vertically interposed between the periphery of the reference platform 32 and the facing portion of the upper face 26.

In order to obtain a reliable verification, it is of the utmost importance than the probe P occupies a very precise and constant position with respect to the outer wall of the final container, and for instance with respect to the portion of the outer wall 29 of the body 28 of a syringe S, i.e. to make sure that the probe P is always at a specified position with respect to the "product" to be "tested".

To this end, the invention provides for an auto-adjustment of the distance "D" between the free upper end 62 of the probe P and the facing portion of the outer wall of the final container.

Figure 6:
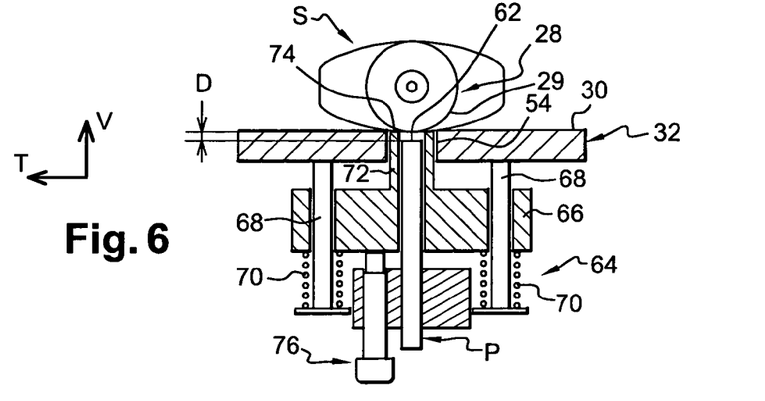
FIG. 6 is a schematic representation of the means holding and precisely positioning the probe with respect to the reference platform.

This function and the associated auto-adjustment means 64 are schematically illustrated at FIG. 6, arranged under the reference platform 32.

The means 64 comprise a probe holder 66 which is vertically slidably mounted with respect to the reference platform 32 here by means of two guiding columns 68. Two adjusting springs 70 are mounted and compressed on the columns 68 in order to permanently urge the probe holder 66 upwardly, and thus the probe P also upwardly.

The probe P occupies a predetermined vertical position with respect to the probe holder 66, and since a free upper end of a tubular prong 72 of the probe holder 66 extends through the hole 54 for having its free annular extremity 74 in contact with the wall 29, then the probe P is moveable with the holder 66 with respect to the reference platform 32 in order that its terminal end 62 occupies the said determined position.

For purpose of calibration, the vertical position of the probe P with respect to the probe holder 66 can also be set, for instance by means of a micrometer screw 76 which can be manually rotated or motorized and controlled by an associated software.

Figure 7A:
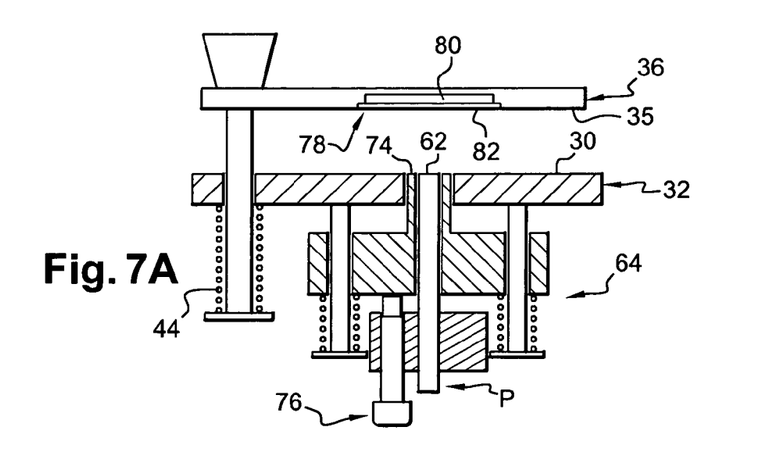
FIGS. 7A and 7B are figures similar to FIG. 6 showing two different embodiments of a reference calibration unit.

For purpose of calibration, and as illustrated at FIG. 7A, the lower face 35 of the clamping bar 36 can be provided with an integrated calibration unit 78 including for instance a polytetrafluoroethylene (PTFE) (Brand name "Teflon") plate 80 and a covering plate 82 made of Poly(methyl methacrylate) (PMMA) (Brand name "Perpex").

Figure 7B:
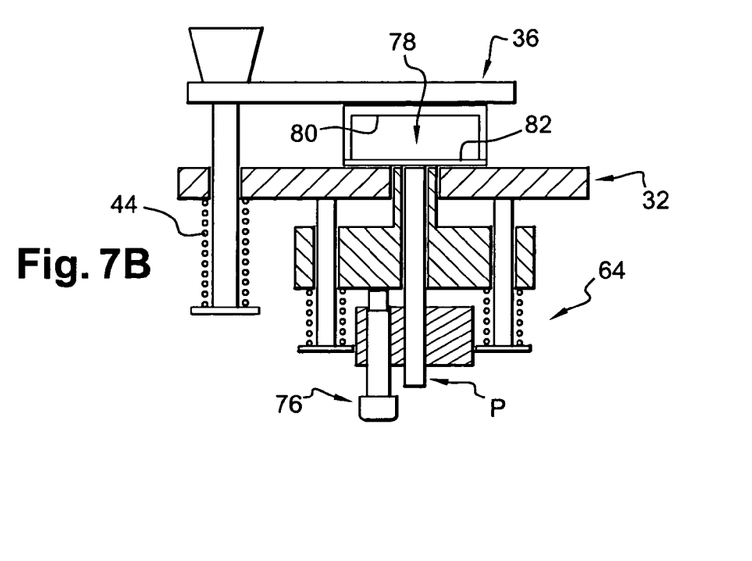

In an alternate design illustrated at FIG. 7B, the reference calibration unit 78 is a removable calibration "box" 78 in the form of a steel case with an internal PTFE coating and a lower cover 82.

The apparatus should be calibrated at the start of every day, to confirm that the system is performing correctly. To calibrate a software is provided in combination with the device, and a calibration sample is presented in a precise manner. The calibration unit is likely to be integrated into the clamping system as illustrated at FIG. 7A. The operator receives confirmation that the results from the calibration analysis are consistent with the expected results, and therefore, the calibration passes.

It is thus possible that the machine would auto-calibrate itself initially as long as the lid is closed and that no product is present in the holding device.

Figure 8:
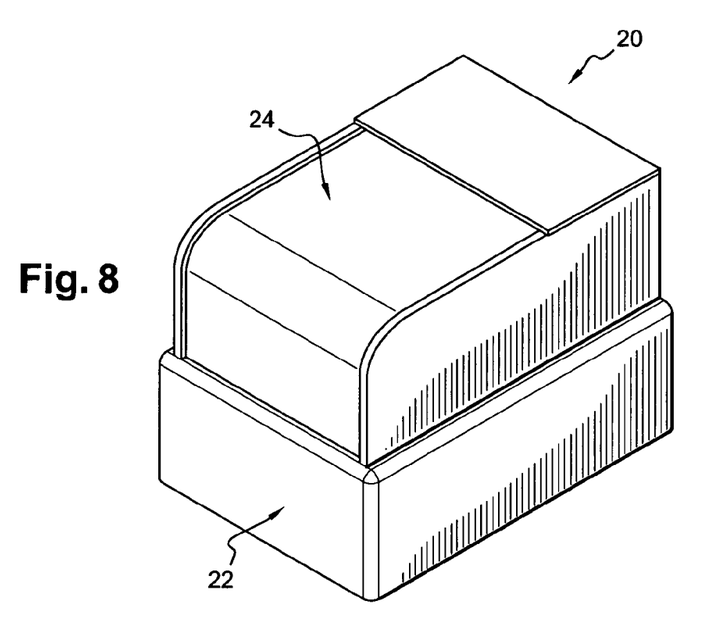
FIG. 8 is a figure similar to FIG. 1 showing an other embodiment of an apparatus according to the invention with an upper sliding lid in its closed position.
Figure 9:
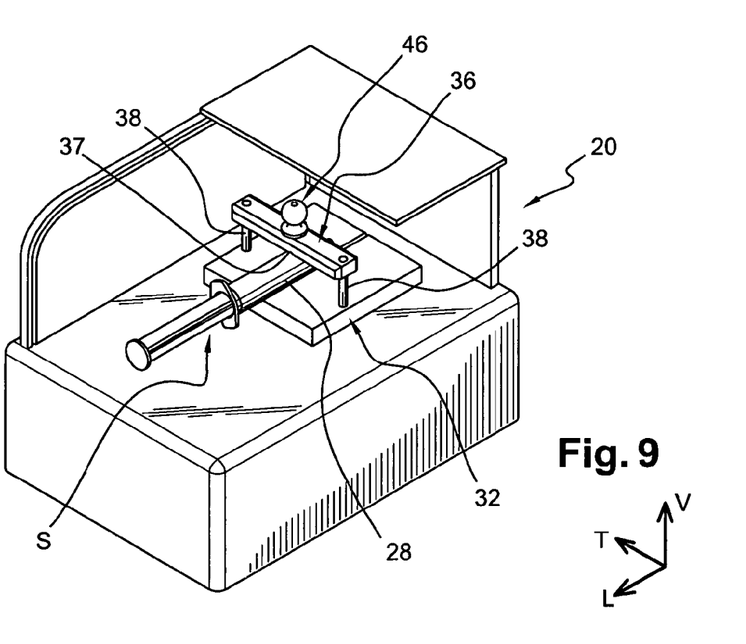
FIG. 9 is a figure similar to FIG. 8 without the lid and a lateral wall and showing a syringe in position on the reference platform and the clamping bar in an upper position.

In the embodiment according to FIGS. 8 and 9, the lid 24 is a sliding lid performing the same functions as the previously described pivoting lid 24.

The clamping bar 36 is here only vertically slidable along two vertical parallel shafts or columns 38, each one equipped with a return spring 44.

Figure 10:
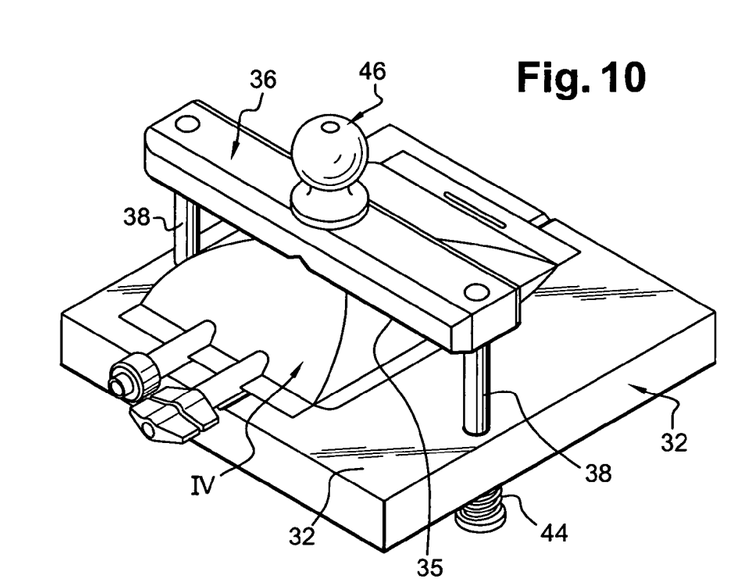
FIG. 10 is a simplified view on an enlarged scale of FIG. 9 showing the clamping system with an IV bag in the verifying position and the clamping bar in its lower work position.
Figure 11:
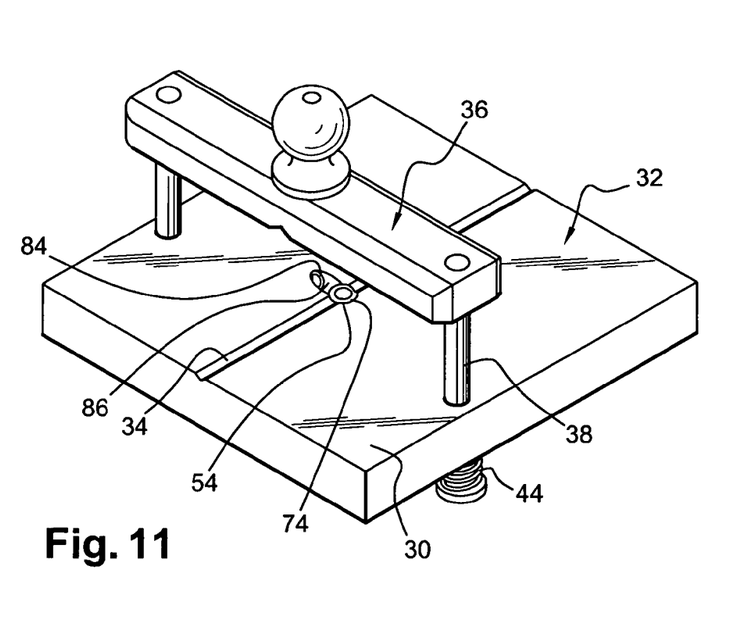
FIG. 11 is a figure similar to FIG. 10 without any final container more clearly showing the reference platform.
Figure 12:
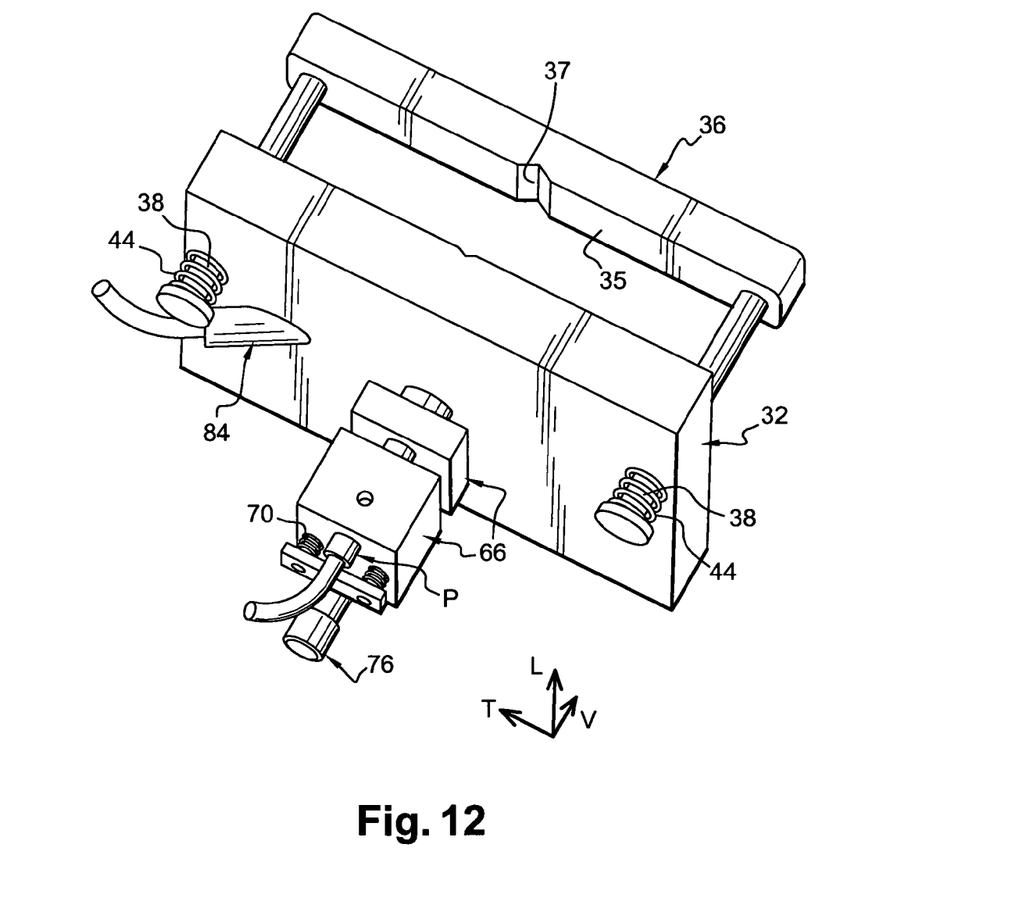
FIG. 12 is an underside perspective view of the arrangement of FIG. 11 more clearly showing some components.

At FIG. 10, the final container 38 is an intravenous Bag or "IV bag" having a semi-flexible body 38 with a portion of its wall 39 in contact and pressed against the upper face 30 of the reference platform 32 in the zone of the through hole 54.

It has also be represented an additional proximity sensor 84 passing through an inclined hole 86 of the reference platform 32 for detecting the presence of a container or sample to be tested and verified.

The spectroscopy device or system used for verification and validation may be Raman or Ultra-Violet or near Infra-Red including:

Light source: a monochromatic laser with an energy power of a variety of power. Such power specifications may be either a fixed attribute of the laser, or the laser may be of a variable power output.

Fibre optic-probe: the fibre optic probe transmits the light from the laser to the sample, and one lead of the probe is therefore connected to the laser. In the event that the light is intended to be transmitted around at 90 degrees, bend, mirrors are incorporated to enable the bend to be transmitted, however there is some loss of the light whenever the fibre optic probe is interrupted by mirrors. The probe head is of a variable focal length that must be selected in order for the beam of laser light to be focused on a point within the sample. When the light is scattered from the sample (using the Raman effect), that scattered light is picked up by a different optical fibre cable within the probe P and is transmitted to the spectrometer where it is analysed and evaluated.

In some embodiments, it is contemplated not to have a fibre optic probe, but using a laser directly into the sample via an optical lens.

In some cases, the probe will include a sharp filter to eliminate the laser wavelength.

Spectrometer: The spectrometer collects the scattered light through a system of grating and slits, to filter out unsuitable scattered light such as light originated from ambient light sources, which is often referred to as "noise". The Raman scattering is picked up on a CCD detector unit. The CCD may be thermoelectrically cooled to minimize extraneous noise generated from prolonged integration times involved with the time the laser light source is presented to the sample.

Data obtained from the received photons on CCD are communicated to a computerized software which displays the resultant signature of scattering effect in a manner that is unique to the molecular structure of the sample being analyzed verified.

Spectrometer Options:

Multiple probe: This option is currently available from the manufacturer of these systems and consists of the ability to collect light scattering at multiple points in a system and to present a laser light source at multiple points. These multiple probes have multiple optical fibre cables that eventually gather into a single collection point which is then transmitted to the collector plates within the spectrometer.

Multiple laser sources: It is contemplated that multiple lasers may be incorporated within a device to provide a variety of power outputs to the sample. Alternatively, the laser output may be at a variable power level which may be controllable by a software.

Colorimeter: It is an other system in addition to the incorporated system which may utilize the emitted colour of a sample to assist in the identification process.

Laser filter: In order to adjust the power for the laser depending on the signature levels.

The spectrometry probe P can preferably be a probe associated with a Raman spectrometer. The optical system spectrometry system comprises a light source, a dispersive system and a detector. The source of irradiation or excitation light and the light sensor are integrated in the probe. The probe also comprises an output module containing optics for delivering an excitation radiation incident beam to the sample and collecting Raman scattered light from the sample. The output focusing lens might be slightly recessed from the terminal end probe such that the focal point of the output focusing lens is in close proximity to the terminal end.

The apparatus according to the invention is designed to verify a product to be the correct drug immediately prior to being administered to the patient.

The invention may be used to verify that the correct chemotherapy medications, compounded drugs, chemotherapy drugs, etc, are properly dispensed to a patient. The invention would primarily function to reduce the rate of errors in dispensing of such medications by verifying and validating medications prior to administration by allowing a pharmacy technician or a nurse to validate the medication administered, in composition and quantity—dosage.

According to a non illustrated aspect of the invention, the system can correlate medication administration information (e.g., time and dosage) by reading a patient bar-coded name bracelet or tag or another readable identifier. Such a scanning device, associated with the verification apparatus, can also be used to scan information associated with the final container, for instance on a tag fixed on the container.

The system associated with the apparatus can also mark the verified and final container with a pass or fail mark. To this end marking means associated with the verification apparatus can print or issue a tag, and/or directly mark an existing tag optically (for instance using the laser beam or a UV light source and a UV sensitive tag), thus recording the results of the analysis).

The unit may include a stamp or printer that applies a mark or label onto containers indicating that the contained product has passed or failed as a match with its supposed content(s). The mark or label is applied before the product is released from the apparatus, so that confusing passed or failed products post the verification process is extremely unlikely.

According to a non illustrated variant, the apparatus may permit an analysis in transversal (T) or longitudinal (L) directions. To this end, the probe might be moving along L or LT axis for multi site analysis (for instance for a drug homogeneity assessment). Alternatively the platform could move in L and/or T, whilst the probe is "stationary".

Figure 13:
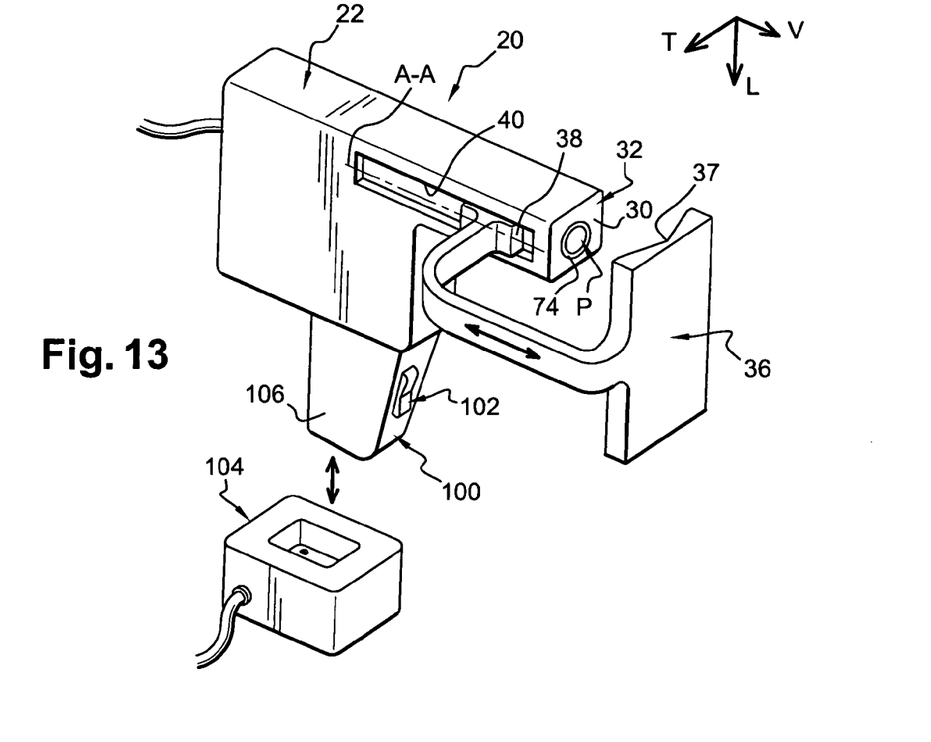
FIG. 13 is a perspective view of an example of an apparatus according to the invention in the form of a portable, stand alone apparatus.

FIG. 13 shows a first embodiment of a portable apparatus 10. The portable or handheld apparatus 10 comprises an enclosing body 22 comprising a lower "pistol-grip" shaped handle 100 by which a user, or a robot arm, may grasp the portable apparatus. The handle is equipped with an activation button 102 for activating the analysis unit to acquire, for instance, a Raman spectrum of a sample. Such an activation element could be replaced by an activation trigger.

The housing 22 supports and houses the probe P and the associated components similar to those previously described in connection with the "desktop" apparatus.

The front face, according to axis V, of the body 22 does constitute the reference plate 32 (which is here integrated to the body 22) of the apparatus 22 which, as previously, is equipped with a movable clamping bar 36.

The clamping bar 36 is slidably movable along the axis A-A with respect to the reference platform and, to this end, comprises a guiding shaft 38 received in a guiding slot 40. Non visible spring means acting on the clamping bar 36 might be arranged inside the housing 22.

The actuation of the clamping bar 36 for "opening" it can be either manual or motorized.

The holding device including the clamping bar 36 facilitates a safe and repeatable position of IV bags, syringes or vials. The holding device is designed such that laser light is not capable of travelling past a protective shield. In conjunction with the protective shield or mask, or as an alternative to the shield, the holding and clamping mechanism may double as a mechanical "shutter" to prevent laser light being exposed whilst no object is being held by the hand held apparatus.

The lower portion 104 of the handle 100 can be received in a receiving base unit 106 for the purpose of supporting it and possibly to permit its connection with a source of current for the charge of a rechargeable battery supply unit included in the portable apparatus.

Load cells or piezoelectric force sensors could be utilised for models containing qualitative functionality.

These load cells or force sensors may be situated within the hand held apparatus, or in the supporting base unit 106, the supporting base unit 106 then including a weighing unit.

The handheld apparatus is an apparatus that permits a) to evaluate the integrity of pharmaceuticals or b) to be used on the bedside level by a nurse.

By design it may incorporate appropriate drug libraries and can be used to check that the pharmaceuticals within a storeroom have not been subject to counterfeiting or inappropriate tampering with the product.

Is a special application of making sure that the product injected into a patient is the right one? The device would check that the product is for the right patient (using barcode on the patient band wrist) at the right time, with the right signatures.

Figure 14:
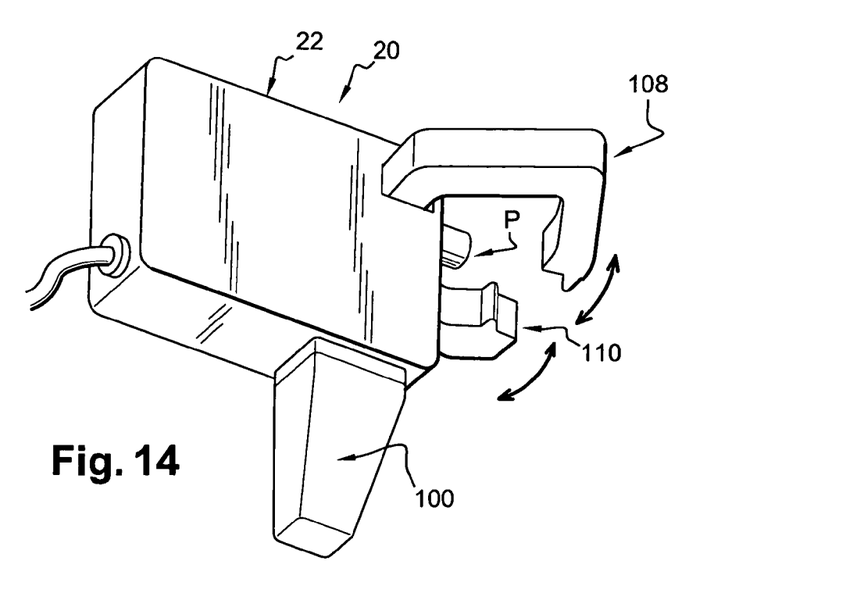
FIG. 14 is a perspective view of another example of an apparatus in the form of a portable, stand alone apparatus In the following description, identical, similar or analogue components will be designated by the same references.

In the embodiment of FIG. 14, the holding device comprises a pair of opposed jaws 108 and 110 which are moveable, for example pivotally around a longitudinal axis) one with respect to the other, and both symmetrically with respect to the body 22.

The two jaws are encompassing a zone or area in registration with the probe P.

Among the pair of jaws which are pivotally mounted on the body 22, one of said jaws ensures the function of a reference platform, and in the other one of said jaws has the function of a clamping bar.

In such an embodiment, the weighing unit might be integrated to the apparatus 20.

Description of a Software for a Nurse or Technician Control a) Driver for the Spectrometer:

The software must be able to turn the device on or off, control the laser and its integration time, and check that safety conditions have been met before turning on the laser.

The software takes then the background noise and uses more than one sample to identify the regular peaks linked to the chemical products.

b) Analysis Software of Signature, Identification:

The software system compares the obtained signature of the sample with signatures of other chemotherapy substances within the library. A match occurs when a sample has a signature of peaks that occur at similar Raman shift wavelengths to a known library substance.

c) Analysis Software of Signature—Chemo-Metrics

Chemo-metrics are used for the quantitative analysis of a sample, providing the concentration value within the sample thru the interaction with several different mathematical modelling formulas that are incorporated within the software.

d) Signature-Data Management:

It is a software process for managing and obtaining signatures from clients, conveying them to a central office for signature validation utilizing a variety of methods including visual inspection and software matching, and then marking the sample for addition to the library upon compiling. When the newly compiled library is completed, it is pushed back to the clients who replace their current library reference file and current quantitative and qualitative models with the new master library file.

e) Manual and Barcode Data entry about the sample to be analyzed—This represents a part of the software which provides a mechanism and prompting of the operator to enter a product description and concentration, perhaps brand of the product, perhaps lot number of the product, total dose being provided in the package, type of package, and another identifier such as patient name, id number, etc.

f) Total Dose Calculator:

The software calculates the total dose of the final drug package based upon the weight that it obtains of the package as it is placed on the tray in the Final Product Handling station. The weight is converted to volume utilizing the density of the product which for most compounds will be 1.0 gm/100 ml, the density of the sterile water.

If the final concentration is identified thru chemo-metrics analysis, one can then take the concentration of the sample, i.e. 50 mg/ml times the total volume of the sample, i.e. 1000 ml, to determine the total dose=50000 mg=50 grams.

g) Database Management System:

It is involved in the event logging software application which records all of the specific pieces of data surrounding the collection and identification and quantification of a sample. This log file can be used to extract reports and evaluate overall system results, errors caught, etc.

h) Interface to Pharmacy System:

The interface to the pharmacy may enable various information to be shared. The first would be to acquire all the information for a specific barcode on the product like patient details, prescribing doctor, drug name and dosage. It would include time and date the product was prepared so that the validity of the product can be checked. The nurse administering the product would be filed into the pharmacy system. If a product is not validated by the device, the interface would automatically inform the pharmacy about the possible error. The pharmacy staff would then be able to be more proactive on errors.

i) Interface to Nurse System Electronic Orders Management System:

The interface to the nurse orders management system may enable various information to be shared. The first would be to acquire all the information for a specific barcode on the product like patient details, prescribing doctor, drug name and dosage. It would check that the pharmacy and nurse system have coherent data. The interface would record when the product was checked, the product signature. It would also check that the drugs being injected at the right time.

How to Calibrate the Machine

The system should be calibrated at the start of every day, to confirm that the system is performing correctly and the spectra being collected can be evaluated. To calibrate a device, there is software within the device, and a calibration sample that is presented to the device in a precise manner. The calibration block is likely to be integrated into the clamping system. The operator receives confirmation the results from the calibration analysis is consistent with the expected results, and therefore, the calibration passes. Calibration is an event which is also logged so that one could confirm the frequency with which the system is calibrated.

How to do Auto-Calibration?

Auto calibration is a process in which the system prompts you to put in a calibration sample at start-up, and the system goes thru the routines automatically. A calibration sample which may be affixed to the product holding clamp in such a manner that it is be positioned properly over the probe when a IV bag or syringe is not present, and the clamp is in a closed position.

How to Make Sure that it is the Right Drug with the Right Quantity for the Right Patient?

The system is used by the nurse before injecting the product into the patient.

The system is to be integrated into the software of the nurse administration system The software would send urgent alerts in case of errors to the nurse manager and to the pharmacy who prepared the dose and to the nurse who is about to administer the medication.

The system would specifically check that it is the right dose for the right patient: Scan the patient ID→Put the dose into machine→Check that the dose is correct with the label barcode data→Inform about the way to administer the product→Make sure it is the right time for administering.

It would check the drug has not been degraded or stayed too long out of the refrigerator or if the product took too long to reach the patient.

The invention claimed is:

1. An apparatus (22) for verifying the identity of a final fluid product for medical or pharmaceutical use, said final product being packaged in a final container (28), said apparatus comprising at least an optical spectroscopy analysis unit adapted to determine at least one property of the final product and for issuing at least a verifying signal corresponding to said property, said unit comprising
a device for holding said final container (28);
a probe (P) associated with a source of light located and configured so as to emit and direct light through the wall (39) of the final container (28) and the final product and comprising a light sensor located so as to receive said directed light after the light has passed through the final product, said sensor providing light sensor signals to be used for the generation of said verifying signal corresponding to said property;
characterized in that said holding device comprises:
a clamping system comprising a reference platform (32) for supporting and positioning the final container (28) in a determined position with respect to the probe (P) and a clamping bar (36) which is moveable with respect to the reference platform (32) for pressing the outer wall (39) of the final container (28) in contact with said reference platform (32), said reference platform (32) being capable of receiving light from said light source, said holding device being adapted to receive any form of final containers such as syringes, vials or intravenous bags, and
characterized in that the clamping bar (36) is pivotally mounted with respect to the reference platform (32), around an axis of rotation (A-A) which is perpendicular to the plane of the reference platform, and characterized in that the clamping bar (36) can pivot between an offset rest angular position for placing the final container (28) on the reference platform (32), and a clamping work angular position in which the clamping (36) bar extends in registration with a facing portion of the wall of the final container.

2. An apparatus according to claim 1, characterized in that the reference platform (32) comprises at least one through hole (54) for the passage of said directed light, and characterized in that said probe (P) is moveable with respect to the reference platform (32) in order that a terminal end (62) of the probe (P) is occupying a determined position with respect to a facing portion of the wall (39) of the final container (28) bearing against the reference platform (32) in the zone of the through hole (54).

3. An apparatus according to claim 2, characterized in that the probe (P) is urged elastically (70) towards the wall of the final container in order to occupy said determined position.

4. An apparatus according to claim 1, characterized in that the clamping bar (36) is urged elastically (28) against the wall of the final container.

5. An apparatus according to claim 1, characterized in that the clamping bar (36) is slidably mounted with respect to the reference platform (32), along a direction (A-A) which is perpendicular to the plane of the reference platform (32).

6. An apparatus according to claim 1, characterized in that the clamping system comprises a device (48, 52) for angularly locking the clamping bar (36) in its clamping work angular position.

7. An apparatus according to claim 1, characterized in that a moveable safety mask (56) is provided which is pivotally linked with the clamping bar (36) and which, when the clamping bar is not in its work angular position, extends on the way of the emitted light.

8. An apparatus according to claim 1, characterized in that the holding device is mounted on a weighing unit (60) in order to determine, directly or indirectly, the weight of the quantity of final product contained in the final container, in order to permit verifying and validating medications prior to their administration by allowing a user to validate the medication administered, in composition and quantity—dosage.

9. An apparatus according to claim 1, characterized in that it comprises a housing having a closed upper part containing at least said holding device and any final container in position for verification.

10. An apparatus according to claim 9, characterized in that the upper part of the housing is equipped with a movable lid (24), and in that the lid is associated with a safety arrangement for interrupting the emission of light by said light source when the lid is not in its closed position.

11. An apparatus according to claim 1 that is configured as a portable, stand alone apparatus having a body comprising a handle (100) by which the user, or a robot arm, may hold it, and an activation element (102).

12. A portable apparatus according to claim 11, characterized in that said probe (P) is supported by said body.

13. A portable apparatus according to claim 12, characterized in that said reference platform (32) is integrated to said body and, and in that said clamping bar (36) is slidably mounted with respect to the reference platform.

14. A portable apparatus according to claim 12, characterized in that it comprises a pair of jaws (108, 110) which are pivotally mounted on said body, in that one of said jaws ensures the function of a reference platform, and in that the other one of said jaws has the function of a clamping bar.

15. An apparatus according to claim 1, characterized in that it includes a device for scanning a barcode, or another readable identifier, associated with a patient and/or associated with the final container.

16. An apparatus according to claim 1, characterized in that it includes a device for marking the verified final container.

17. An apparatus according to claim 1, characterized in that it includes means for displacing the final container with respect to the probe for providing several various light sensor signals for the generation of the said signal corresponding to said property.

18. An apparatus according to claim 1, characterized in that said analysing unit is using the Raman effect in order to obtain a Raman spectrum of the final product.

* * * * *